US009327459B2

(12) United States Patent
Okuda et al.

(10) Patent No.: US 9,327,459 B2
(45) Date of Patent: May 3, 2016

(54) METHOD FOR PRODUCING STRETCHABLE SHEET

(75) Inventors: Jun Okuda, Kagawa (JP); Satoshi Mitsuno, Kagawa (JP)

(73) Assignee: Unicharm Corporation, Ehime (JP)

( * ) Notice: Subject to any disclaimer, the term of this patent is extended or adjusted under 35 U.S.C. 154(b) by 219 days.

(21) Appl. No.: 14/008,644

(22) PCT Filed: Mar. 26, 2012

(86) PCT No.: PCT/JP2012/057780
§ 371 (c)(1),
(2), (4) Date: Sep. 30, 2013

(87) PCT Pub. No.: WO2012/133330
PCT Pub. Date: Oct. 4, 2012

(65) Prior Publication Data
US 2014/0225308 A1    Aug. 14, 2014

(30) Foreign Application Priority Data

Mar. 31, 2011    (JP) .................................. 2011-080366

(51) Int. Cl.
| | |
|---|---|
| *D06C 3/06* | (2006.01) |
| *B29D 7/01* | (2006.01) |
| *D06C 23/04* | (2006.01) |
| *A61F 13/49* | (2006.01) |
| *A61F 13/15* | (2006.01) |

(52) U.S. Cl.
CPC ............ *B29D 7/01* (2013.01); *A61F 13/15593* (2013.01); *A61F 13/15707* (2013.01); *A61F 13/49009* (2013.01); *D06C 3/06* (2013.01); *D06C 23/04* (2013.01)

(58) Field of Classification Search
CPC ............................ A61F 13/15707; D06C 3/06
See application file for complete search history.

(56) References Cited

U.S. PATENT DOCUMENTS

| | | | |
|---|---|---|---|
| 4,223,059 A | 9/1980 | Schwarz | |
| 5,167,897 A | 12/1992 | Weber et al. | |
| 5,455,992 A * | 10/1995 | Kurschatke | ............ B29C 55/08 26/87 |
| 6,506,329 B1 | 1/2003 | Curro et al. | |
| 2008/0124996 A1 | 5/2008 | Hashimoto et al. | |
| 2013/0031813 A1* | 2/2013 | Ishikawa | .................. D06C 3/06 38/44 |

FOREIGN PATENT DOCUMENTS

| | | |
|---|---|---|
| JP | 2002-501125 A | 1/2002 |
| JP | 2002-501128 A | 1/2002 |
| JP | 3516679 B2 | 1/2004 |
| JP | 2008-081849 A | 4/2008 |
| JP | 2008-169506 A | 7/2008 |
| WO | WO 99/37830 A1 | 7/1999 |
| WO | WO 00/69383 A1 | 11/2000 |
| WO | WO 2008/066009 | 6/2008 |

OTHER PUBLICATIONS

International Search Report from corresponding PCT application No. PCTJP2012/057780 dated Jun. 19, 2012 (2 pgs).

* cited by examiner

*Primary Examiner* — Ryan Ochylski
(74) *Attorney, Agent, or Firm* — Brinks Gilson & Lione (57) ABSTRACT

A method for producing a stretchable sheet that can uniform the shape, such as the width and thickness, and the strength, of a stretched nonwoven fabric. The method for producing a stretchable sheet according to the invention comprises a step of stretching a nonwoven fabric in the cross-machine direction perpendicular to the machine direction in which the nonwoven fabric is transported and a step of compressing the nonwoven fabric stretched in the step of stretching the nonwoven fabric, in the thickness direction of the nonwoven fabric.

19 Claims, 11 Drawing Sheets

METHOD FOR PRODUCING STRETCHABLE SHEET

RELATED APPLICATION

This application is a 35 U.S.C. §371 national phase filing of International Patent Application No. PCT/JP2012/057780, filed Mar. 26, 2012, through which and to which priority is claimed under 35 U.S.C. §119 to Japanese Patent Application No. 2011-080366, filed Mar. 31, 2011.

TECHNICAL FIELD

The present invention relates to a method for producing a stretchable sheet.

BACKGROUND ART

For formation of elasticized waist bands and/or leg bands into disposable diapers, a method is known in the prior art, in which a laminate web used for production of a disposable diaper is stretched to impart elasticity to the web (PTL 1, for example). According to this method, in a step of incrementally stretching an unstretched laminate web, both the peripheral edge portions of a first elastomer layer and an extendable second layer are restrained so that the extendable second layer is permanently stretched by incremental stretching, in such a manner that the width of the laminate web in the stretching direction is the same as before application of stretching. Also, the pressure device used for stretching of the laminate web comprises a pair of corrugated rolls whose rotational axis lines are perpendicular to the movement direction of the web, the corrugated rolls having undulating three-dimensional surfaces, and the pair of corrugated rolls engaging each other when the unstretched laminated web passes between them. Also, by holding both the peripheral edge portions elastically, by holding both the peripheral edge portions with a pair of freely elastic deformable disks situated on the corrugated rolls, or by holding both the peripheral edge portions with a pair of continuous belts situated on the corrugated rolls, both the peripheral edge portions of the first elastomer layer and the extendable second layer are restrained.

According to the method for imparting elasticity to the web as described in PTL 1, when a portion of the web to be used for production of a disposable diaper passes between the pair of corrugated rolls, it is possible to prevent sliding and contraction of the web in the direction parallel to the direction of stretching of the web.

CITATION LIST

Patent Literature

[PTL 1] Japanese Patent Publication No. 3516679

DISCLOSURE OF THE INVENTION

Technical Problem

In a method for imparting elasticity to a web such as described in PTL 1, however, the irregularities produced during stretching remain even after stretching, and therefore wrinkles are produced in the machine direction in which the web advances, often resulting in waviness in the web. Consequently, a problem occurs in that it is often impossible to stably accomplish a step of transporting the stretched web, and to stably accomplish processing such as folding, cutting and attaching the stretched web in subsequent steps. For example, when the stretched web is directly cut and attached to another sheet, the stretched section of the stretched web curls up and is often difficult to attach to the other sheet.

Solution to Problem

As a result of earnest investigation, the present inventors have found that when the shape, such as width and thickness, and strength of a stretched nonwoven fabric are non-uniform, it is not possible to stably transport the stretched nonwoven fabric and to stably process it in a subsequent step. In order to solve the aforementioned problems, therefore, the invention has the following feature(s).

Specifically, the invention relates to a method for producing a stretchable sheet from a nonwoven fabric, the method comprising: a step of stretching the nonwoven fabric in the cross-machine direction perpendicular to the machine direction in which the nonwoven fabric is transported; and a step of compressing the nonwoven fabric stretched in the step of stretching the nonwoven fabric, in the thickness direction of the nonwoven fabric.

Effect of the Invention

According to the invention, it is possible to uniform the shape, such as the width and thickness, and the strength, of a stretched nonwoven fabric. This allows the stretched nonwoven fabric to be stably transported and stably processed in a subsequent step.

DESCRIPTION OF EMBODIMENTS

The invention will now be described with reference to the accompanying drawings, with the understanding that the invention is not limited to the examples depicted in the drawings.

Figure 1:
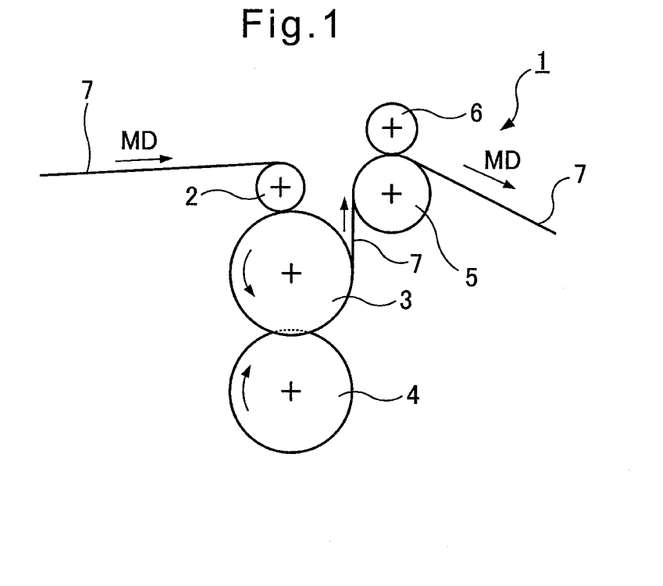
FIG. 1 is a diagram for illustration of a stretching apparatus to be used for a method for producing a stretchable sheet according to an embodiment of the invention.

A method for producing a stretchable sheet according to an embodiment of the invention will now be explained with reference to FIG. 1. FIG. 1 is a diagram for illustration of a stretching apparatus 1 to be used for a method for producing a stretchable sheet according to an embodiment of the invention. The stretching apparatus 1 comprises a transport roll 2, an upper stretching roll 3, a lower stretching roll 4, a heating roll 5 and a press roll 6. In the method for producing a stretchable sheet according to one embodiment of the invention, a nonwoven fabric 7 is stretched by the upper stretching roll 3 and lower stretching roll 4, and then the nonwoven fabric 7 is heated and compressed by the heating roll 5 and press roll 6. The method for producing a stretchable sheet according to an embodiment of the invention will now be explained in detail.

First, the nonwoven fabric 7 transported to the stretching apparatus 1 passes through the transport roll 2, and is wound around the upper stretching roll 3.

The nonwoven fabric 7 to be used for production of a stretchable sheet is one that exhibits or increases stretchability in the stretching step described below. The nonwoven fabric to be stretched is, for example, a nonwoven fabric composed of extensible (elongatable) fibers and stretchable fibers. The term "stretchable fibers" refers to fibers that are elastically extendable, and the term "extensible fibers" refers to fibers that are generally non-elastically extendable. Thus, extensible fibers may also be fibers that undergo plastic deformation with less elongation than elongation at the elastic limit of the stretchable fibers. The nonwoven fabric 7 may also be a combined filament type nonwoven fabric produced by mixing extensible fibers and stretchable fibers, or it may be a laminated type nonwoven fabric with an extensible fiber layer and an stretchable fiber layer, which are stacked as separate layers.

Thermoplastic polyolefin fibers may be mentioned as examples of extensible fibers. Thermoplastic elastomer fibers may be mentioned as examples of stretchable fibers. Thermoplastic polyolefin fibers are, for example, simple polypropylene fibers or polyester fibers, or composite fibers with a core-sheath structure comprising polypropylene or polyester. Thermoplastic elastomer fibers are, for example, polyurethane fibers or polystyrene-based fibers.

The method of forming the nonwoven fabric may be a spunbond method or thermal bond method. The basis weight and fiber size of the nonwoven fabric are appropriately selected in the range of 20-150 g/m$^2$ and the range of 10 to 30 respectively, and the mixing ratio of the extensible fibers to stretchable fibers is appropriately selected in the range of 10-90%.

The nonwoven fabric 7 passes through the transport roll 2 situated above the upper stretching roll 3, and is wound around the upper stretching roll 3. This lengthens the distance over which the nonwoven fabric 7 contacts with the upper stretching roll 3. Also, friction force between the nonwoven fabric 7 and the upper stretching roll 3 is increased, and it is possible to prevent the nonwoven fabric 7 from meandering in the cross-machine direction perpendicular to the machine direction (MD) that corresponds to the transport direction of the nonwoven fabric 7, as well as forming wrinkles in the machine direction and thereby contracting.

In addition, in the method for imparting elasticity to a web described in PTL 1, a holder such as a disc or continuous belt was used to restrain both peripheral edge portions of the web, in order to prevent the web from meandering and contracting in the cross-machine direction. Consequently, if the holder becomes worn, the restraining force with which both peripheral edge portions of the web are restrained may vary, and thus the web may meander. With the embodiment of the invention, however, it is possible to inhibit meandering and contraction in the cross-machine direction without using such a holder, and therefore the problem due to abrasion of the holder does not occur.

In order to increase friction force between the nonwoven fabric 7 and the upper stretching roll 3, a material with high friction force such as rubber may be used as a material for a portion of the outer periphery of the upper stretching roll 3, which corresponds to the non-convexity-formed sections 42 of the lower stretching roll 4 described below.

The nonwoven fabric 7 may be heated by a heating roll or hot air apparatus (not shown) located upstream of the transport roll 2. For example, a heating roll (not shown) may be heated to 80° C., thereby raising the temperature of the nonwoven fabric 7 passing through the transport roll 2 to approximately 50° C. This will allow the nonwoven fabric 7 to be stretched more uniformly in the cross-machine direction during the stretching step described below.

Figure 2:
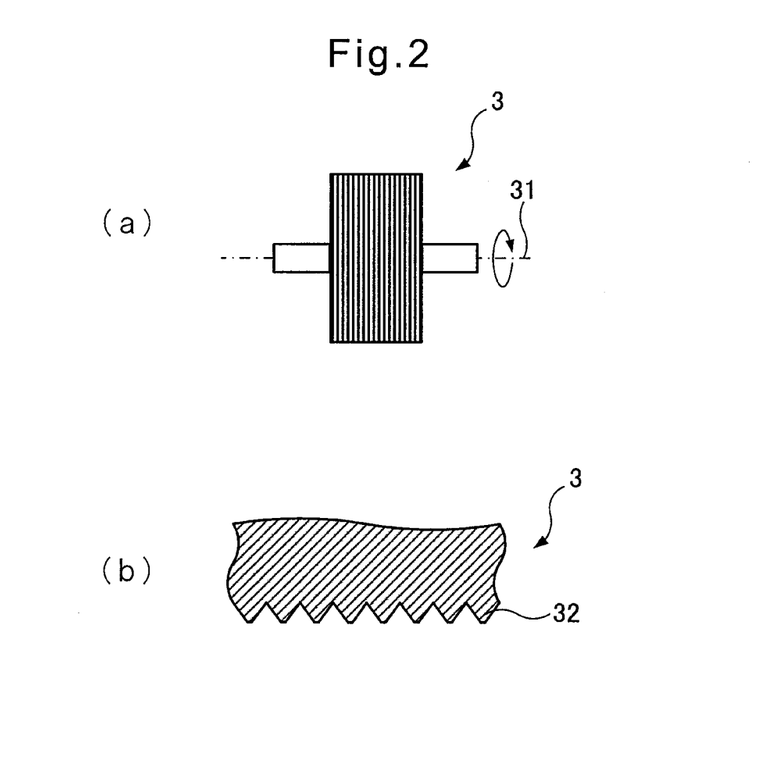
FIG. 2 is a diagram for illustration of an upper stretching roll.

As shown in FIG. 2, the upper stretching roll 3 is a tooth/groove roll which has a plurality of convex parts 32 formed on the outer peripheral surface and extending in the rotational direction around the rotating shaft 31 of the upper stretching roll 3. The shapes of the convex parts 32 are roughly triangular, in a cross-section along the direction of the rotating shaft of the upper stretching roll 3. Also, the outer surface of the upper stretching roll 3 is polished and the tips of the convex parts 32 are flattened. The cross-sectional shapes of the convex parts 32 in the direction of the rotating shaft of the upper stretching roll 3 are not limited to being roughly triangular, and may instead be rectangular, trapezoid, semicircular or the like. The outer periphery of the upper stretching roll 3 may be formed of ferrite-based stainless steel (SUS430 2B), for example. Also, the upper stretching roll 3 may be heated in order to allow more uniform stretching of the nonwoven fabric 7 in the cross-machine direction during the stretching step described below.

Next, as shown in FIG. 1, the nonwoven fabric 7 wound around the upper stretching roll 3 is transported between the upper stretching roll 3 and the lower stretching roll 4, and passes between the upper stretching roll 3 and the lower stretching roll 4.

Figure 3:
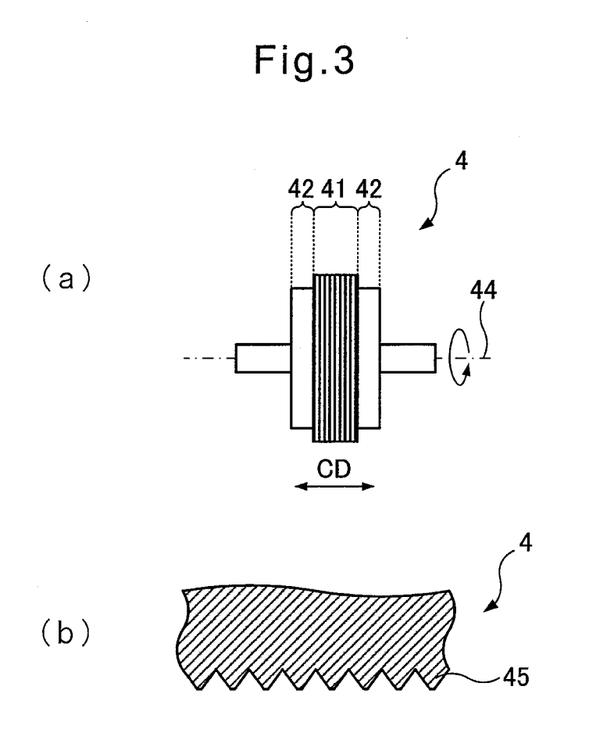
FIG. 3 is a diagram for illustration of a lower stretching roll.

As shown in FIG. 3, the lower stretching roll 4 has a convexity-formed section 41 and non-convexity-formed sections 42, which are arranged in the direction of the rotating shaft 44 of the lower stretching roll 4. The non-convexity-formed sections 42 are provided on both sides in the cross-machine direction (CD) of the convexity-formed section 41. On the outer peripheral surface of the convexity-formed section 41 of the lower stretching roll 4, there are formed a plurality of convex parts 45 extending in the rotational direction around the rotating shaft 44 of the lower stretching roll 4. Thus, the lower stretching roll 4 is also a tooth/groove roll, similar to the upper stretching roll 3. The shapes of the convex parts 45 in a cross-section along the direction of the rotating shaft of the lower stretching roll 4 are roughly triangular, similar to the upper stretching roll 3. The cross-sectional shapes of the convex parts 45 in the axial direction of the lower stretching roll 4 are not limited to being roughly triangular, so long as the convex parts 45 of the lower stretching roll 4 are formed so as to fit with the convex parts 32 of the upper stretching roll 3.

As shown in FIG. 3, no convex parts 45 are formed in the non-convexity-formed sections 42 of the lower stretching roll 4. Also, the diameter of the lower stretching roll 4 in the non-convexity-formed sections 42 is smaller than the diameter of the lower stretching roll 4 in the convexity-formed section 41.

The outer periphery of the lower stretching roll 4 may be formed of ferrite-based stainless steel (SUS430 2B), for example. Also, the lower stretching roll 4 may be heated in order to allow more uniform stretching of the nonwoven fabric 7 in the cross-machine direction during the stretching step.

Figure 4:
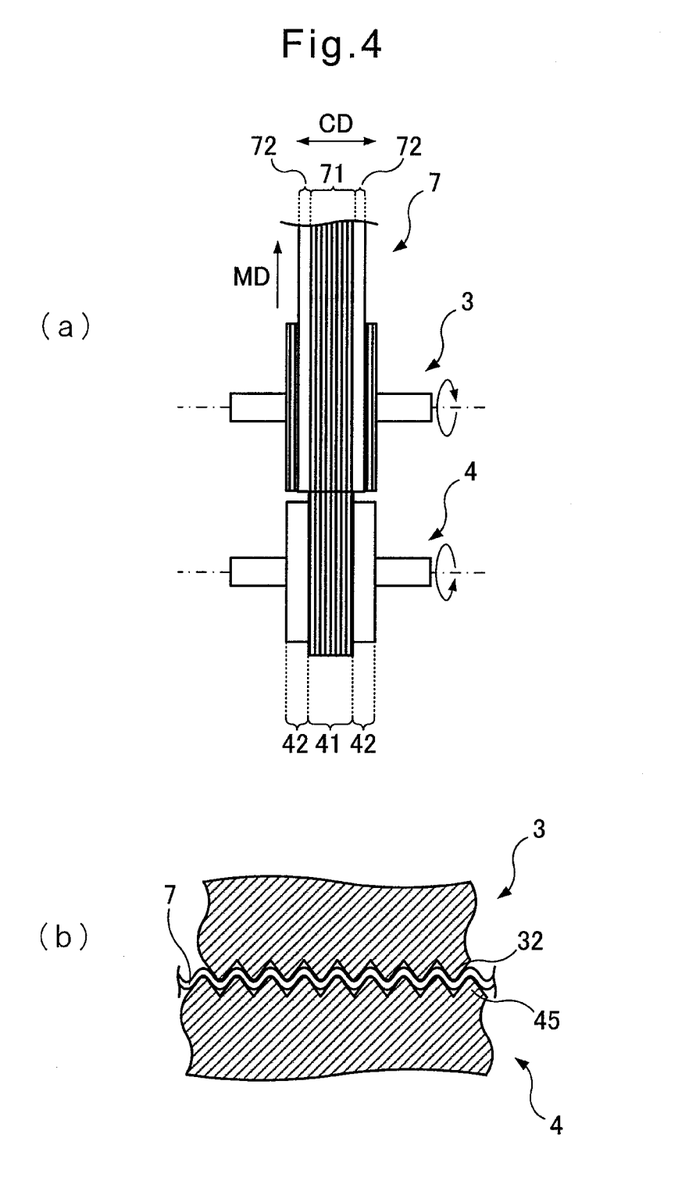
FIG. 4 is a diagram for illustration of stretching of a nonwoven fabric by an upper stretching roll and a lower stretching roll.

As shown in FIG. 4(a), the nonwoven fabric 7 passes between the upper stretching roll 3 and the convexity-formed section 41 and non-convexity-formed sections 42 of the lower stretching roll 4. As shown in FIG. 4(b), the convex parts 32 of the upper stretching roll 3 and the convex parts 45 of the lower stretching roll 4 engage with each other between the upper stretching roll 3 and the convexity-formed section 41 of the lower stretching roll 4. The nonwoven fabric 7 is stretched in the cross-machine direction (CD), by passing through the gap between the pair of rolls 3, 4 having the convex parts 32, 45 formed on the outer peripheral surface and extending in the rotational direction, the convex parts 32, 45 of the rolls 3, 4 being engaged with each other so that the rolls 3, 4 rotate. Also, since the upper stretching roll 3 is separated from the lower stretching roll 4 by a longer distance between the upper stretching roll 3 and the non-convexity-formed sections 42 of the lower stretching roll 4, the nonwoven fabric 7 is not stretched between the upper stretching roll 3 and the non-convexity-formed sections 42 of the lower stretching roll 4. Thus, as shown in FIG. 4(a), a stretched section 71 stretched in the cross-machine direction (CD) is formed at the center of the nonwoven fabric 7 passed between the upper stretching roll 3 and the lower stretching roll 4, and unstretched sections 72 that are unstretched are formed on both sides of the stretched section 71 in the cross-machine direction.

The formation pitch of the convex parts 32, 45 of the upper stretching roll 3 and lower stretching roll 4 is preferably selected within the range of 1-5 mm, and is, for example, 2.5 mm. Also, the width of the flat portions at the tips of the convex parts 32, 45 is preferably selected between 0.01 and 1 mm, and is, for example, 0.1 mm. The engagement depth of the convex parts 32 of the upper stretching roll 3 and the convex parts 45 of the lower stretching roll 4 is preferably selected between 1 and 20 mm, and is, for example, 2.8 mm. The outer diameter of the upper stretching roll 3 is preferably selected in the range of 50 to 500 mm, and is, for example, 150 mm. The outer diameter of the convexity-formed section 41 of the lower stretching roll 4 is preferably selected in the range of 50 to 500 mm, and is, for example, 150 mm.

Next, as shown in FIG. 1, the stretched nonwoven fabric 7 passes between the heating roll 5 and the press roll 6. The heating roll 5 and press roll 6 are flat rolls having smooth outer peripheral surfaces. Also, the outer periphery of the press roll 6 may be made of an elastic material such as rubber or a silicon resin.

The heating roll 5 and press roll 6 can also impart tensile force to the stretched nonwoven fabric 7 in the machine direction (MD). This can accomplish effective stretching by increasing the friction force between the upper stretching roll 3 and the nonwoven fabric 7.

When tensile force is applied to the stretched nonwoven fabric, the tensile force applied to the stretched nonwoven fabric becomes less uniform due to imbalances in the strength and stiffness of the nonwoven fabric caused by stretching, and thus the stretched nonwoven fabric forms wrinkles and curls up. Such wrinkles and curling up can cause the stretched nonwoven fabric to exhibit a high degree of meandering. Consequently, it may be preferred not to apply tensile force to the stretched nonwoven fabric, in order to prevent a high degree of meandering. However, if no tensile force is applied to the stretched nonwoven fabric, this may lead to processing defects such as transfer failures or cutting failures caused by meandering, in a subsequent step of transferring other members to the stretched nonwoven fabric or cutting the stretched nonwoven fabric. Therefore, the tensile force applied by the heating roll 5 and press roll 6 to the nonwoven fabric 7 passed between the upper stretching roll 3 and the lower stretching roll 4, is preferably a tensile force such that a transport ratio of the nonwoven fabric 7 is between 1.00 and 1.10 when it passes between the upper stretching roll 3 and the lower stretching roll 4. If the transport ratio of the nonwoven fabric 7 is smaller than 1.00, the reduced friction force between the nonwoven fabric 7 and the upper stretching roll 3 will cause increased sliding of the nonwoven fabric 7 in the direction perpendicular to the machine direction, often resulting in stretching failures, and if the transport ratio of the nonwoven fabric 7 is larger than 1.10, the aforementioned wrinkles and curling up will become extreme, often making it difficult to prevent meandering of the stretched nonwoven fabric even by the step of compressing the stretched nonwoven fabric, explained below. The transport ratio referred to here is calculated by dividing a transport speed by a supply speed.

The relationship between the transport ratio of the nonwoven fabric in the stretching step and the width of the nonwoven fabric and meandering in the cross-machine direction will now be explained with reference to FIGS. 5 to 8. Using a nonwoven fabric with a width of 62 mm and a basis weight of 70 g/m$^2$, the relationship between the transport ratio of the nonwoven fabric and the width and meandering in the cross-machine direction of the nonwoven fabric was examined. The formation pitch for the convex parts 32, 45 of the upper stretching roll 3 and lower stretching roll 4 used for the stretching step was 2.5 mm, the width of the flat portions at the tips of the convex parts 32, 45 was 0.1 mm, the engagement depth between the convex parts 32 of the upper stretching roll 3 and the convex parts 45 of the lower stretching roll 4 was 2.8 mm, and the outer diameter of the upper stretching roll 3 and the outer diameter of the lower stretching roll 4 at the convexity-formed section 41 were 150 mm. The circumferential speed of the upper stretching roll 3 and lower stretching roll 4 was 100 m/min.

The width of the nonwoven fabric 7 was calculated from an image of the photographed nonwoven fabric, taken by a video camera on the nonwoven fabric 7 ejected from between the upper stretching roll 3 and the lower stretching roll 4. The meandering of the nonwoven fabric in the cross-machine direction was examined by measuring positions of both side edge parts of the photographed nonwoven fabric, calculating the center of those positions, i.e. the gravity center position of the nonwoven fabric, and determining the meandering state of the nonwoven fabric from variation in the calculated gravity center position. A larger meandering of the nonwoven fabric 7 results in a larger variation in the calculated gravity center position. The widths and gravity center positions were examined at 100 locations of the nonwoven fabric, for a transport ratio of 1.00 and a transport ratio of 1.02.

Figure 5:
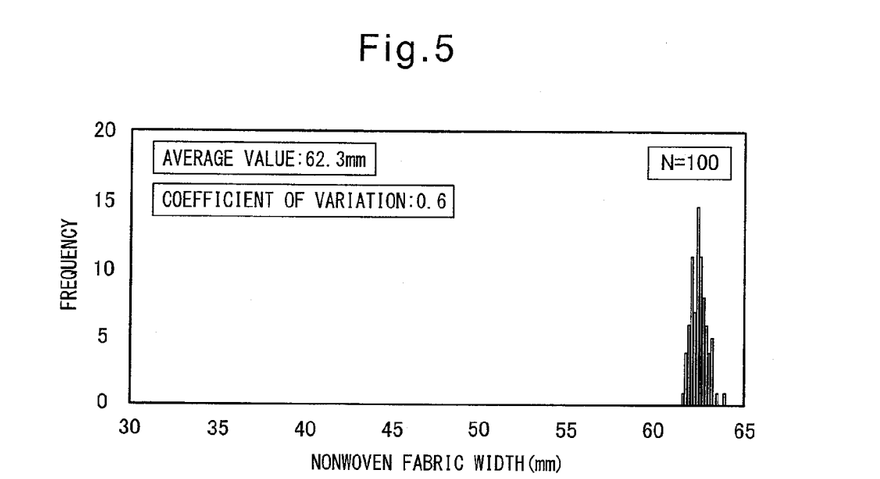
FIG. 5 is a graph showing the width distribution of a nonwoven fabric stretched at a transport ratio of 1.00.
Figure 6:
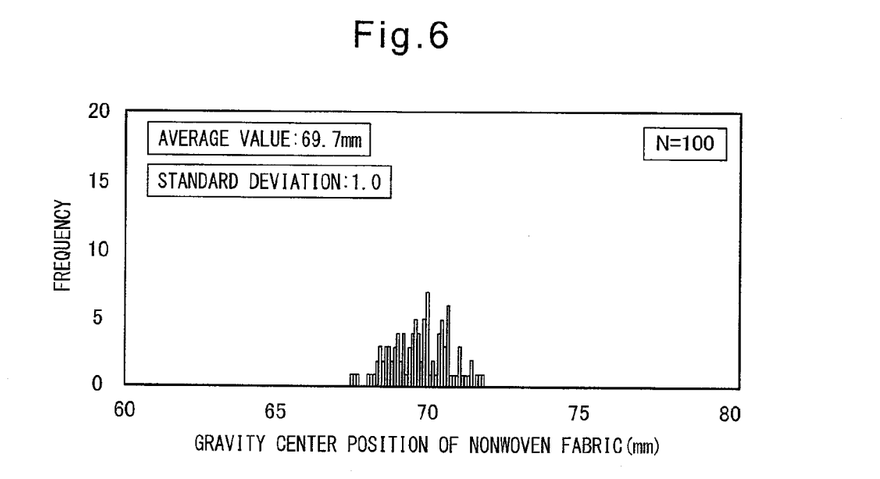
FIG. 6 is a graph showing the gravity center position distribution of a nonwoven fabric stretched at a transport ratio of 1.00.

FIG. 5 is a graph showing the width distribution of 100 measurement locations of a nonwoven fabric stretched at a transport ratio of 1.00. The average value of the measured widths of the nonwoven fabric was 62.3 mm, and the coefficient of variation was 0.6. The coefficient of variation is calculated by dividing the standard deviation by the average value. A smaller coefficient of variation corresponds to a lower variation in value. FIG. 6 is a graph showing the gravity center position distribution of 100 measurement locations of a nonwoven fabric stretched at a transport ratio of 1.00. The average value of the measured gravity center positions of the nonwoven fabric was 69.7 mm, and the standard deviation was 1.0.

Figure 7:
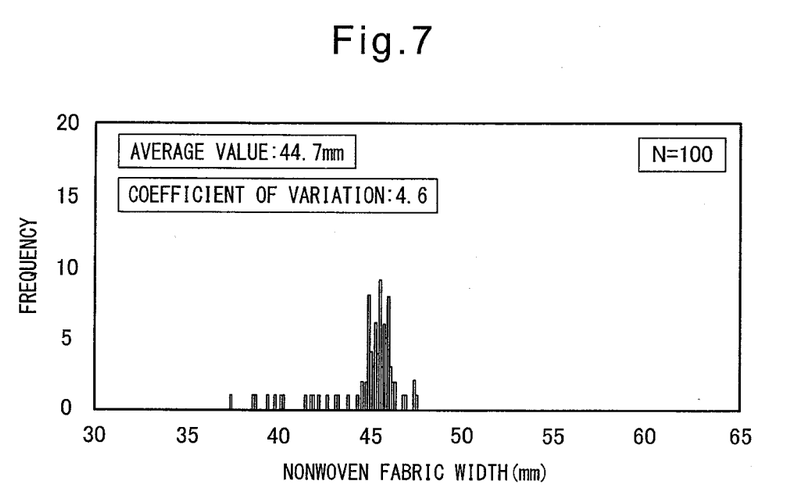
FIG. 7 is a graph showing the width distribution of a nonwoven fabric stretched at a transport ratio of 1.02.

FIG. 7 is a graph showing the width distribution of 100 measurement locations of a nonwoven fabric stretched at a transport ratio of 1.02. The average value of the measured widths of the nonwoven fabric was 44.7 mm, and the coefficient of variation was 4.6. In comparison with the value when the transport ratio was 1.00 (see FIG. 5), it is seen that application of tensile force to the nonwoven fabric in the machine direction resulted in a narrower width of the nonwoven fabric and a larger variation in the nonwoven fabric width. This was because application of tensile force to the nonwoven fabric in the machine direction produced wrinkles in the nonwoven fabric in the machine direction.

Figure 8:
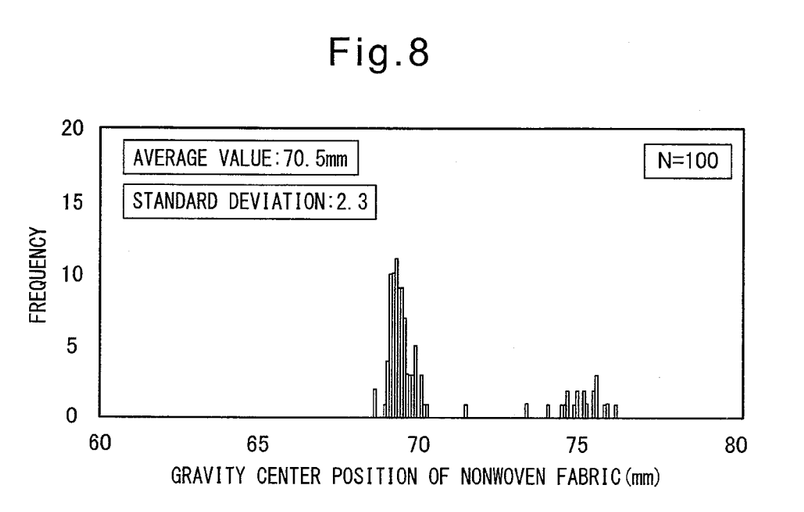
FIG. 8 is a graph showing the gravity center position distribution of a nonwoven fabric stretched at a transport ratio of 1.02.

FIG. 8 is a graph showing the gravity center position distribution of 100 measurement locations of a nonwoven fabric stretched at a transport ratio of 1.02. The average value of the measured gravity center positions of the nonwoven fabric was 70.5 mm, and the standard deviation was 2.3. In comparison with the value when the transport ratio was 1.00 (see FIG. 6), it appears that application of tensile force to the nonwoven fabric in the machine direction resulted in increased meandering of the nonwoven fabric. However, when the gravity center position distribution of the nonwoven fabric shown in the graph of FIG. 6 is compared with the gravity center position distribution of the nonwoven fabric shown in the graph in FIG. 8, it is seen that most of the gravity center positions of the nonwoven fabric is near a value of 69 mm, with low variation, and that applying tensile force to the nonwoven fabric in the machine direction reduces meandering of the nonwoven fabric.

However, as shown in the graph of FIG. 8, several of the gravity center positions of the nonwoven fabric significantly deviated from the vicinity of 69 mm. This is thought to contribute to an increase in the standard deviation of the gravity center positions of the nonwoven fabric. This is attributed to wrinkle formation in the nonwoven fabric in the machine direction due to stretching, which leads to formation of non-uniform portions in the nonwoven fabric, and sometimes produces a large meandering. Consequently, if the stretched nonwoven fabric is made uniform by preventing formation of wrinkles, this will prevent a large meandering that sometimes occurs, and lead to no gravity center position significantly deviated from the vicinity of 69 mm, and significant reduction of the standard deviation of the gravity center positions of the nonwoven fabric. According to one embodiment of the invention, the heating roll 5 and press roll 6 apply tensile force to the nonwoven fabric, as well as compress and heat the nonwoven fabric as explained below, and therefore the stretched nonwoven fabric becomes uniform and meandering of the nonwoven fabric is minimized.

The heating roll 5 and press roll 6 compress the nonwoven fabric 7 in the thickness direction. This allows the shape, such as width and thickness of the stretched nonwoven fabric 7 to be uniform, and also allows the stretched nonwoven fabric 7 to be stably transported and stably processed in a subsequent step. In particular, among a stretched section 71 with low stiffness and unstretched sections 72 with high stiffness, which are formed in the nonwoven fabric 7, the stretched section 71 with low stiffness is more prone to curling up, and therefore it is difficult to be stably transported and stably processed in a subsequent step. Consequently, the effect obtained from compression of the nonwoven fabric 7 in the thickness direction by the heating roll 5 and press roll 6, i.e., stable transport of the stretched nonwoven fabric 7 and stable processing in a subsequent step, is particularly notable for a partially stretched nonwoven fabric.

The pressure applied to the nonwoven fabric 7 by the heating roll 5 and press roll 6 is preferably a linear pressure of 1 N/10 mm or greater, more preferably 1-100 N/10 mm and even more preferably 10-50 N/10 mm. If the linear pressure applied to the nonwoven fabric 7 is less than 1 N/10 mm, variation may occur in the thickness and width of the nonwoven fabric 7, and thus wrinkles may be formed in the nonwoven fabric 7 in the machine direction, often making it impossible to accomplish stable transport of the stretched nonwoven fabric or stable processing in a subsequent step. If the linear pressure applied to the nonwoven fabric 7 is greater than 100 N/100 mm, the press roll 6 may become prone to wear and stable compression may not be possible. The linear pressure is calculated by dividing the load on the roll by the width of the roll, and for example, when two pressing cylinders are used to apply pressure from the press roll 6 to the nonwoven fabric 7, the linear pressure applied to the nonwoven fabric can be calculated by the following formula:

Linear pressure of press roll 6 (N/10 mm)=0.98×{π× $(d/2)^2$×2γP−G}/W wherein, d is the inner diameter of the pressing air cylinder (not shown) of the press roll 6, γ is the lever ratio of the pressing mechanism, P is the gauge pressure (kgf/cm$^2$) supplied to the pressing air cylinder (not shown) of the press roll 6, G is the weight (kg) of the press roll 6 and W is the width (cm) of the press roll 6.

The relationship between the linear pressure applied by the heating roll 5 and press roll 6, and the thickness of the nonwoven fabric 7 compressed by the heating roll 5 and press roll 6, will now be explained with reference to the graph in FIG. 9. The nonwoven fabric stretched at a transport ratio of 1.02 as described above was passed between the heating roll 5 and the press roll 6, and the thickness of the nonwoven fabric 7 was measured.

Figure 10:
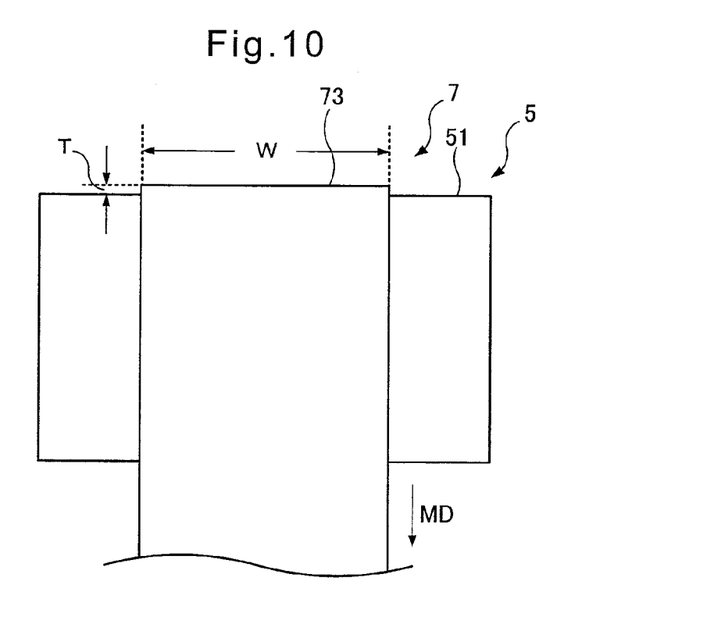
FIG. 10 is a diagram for illustration of a method of measuring the width and thickness of a nonwoven fabric.

As shown in FIG. 10, the nonwoven fabric 7 contacting the outer peripheral surface 51 of the heating roll 5 was photographed with a video camera, and the difference T between the height of the top side 73 of the nonwoven fabric 7 and the height of the outer peripheral surface 51 of the heating roller 5 was calculated from the photographed image, to measure the thickness of the nonwoven fabric 7. The nonwoven fabric 7 was compressed using the heating roller 5 which was unheated. The thickness of the nonwoven fabric was examined at 100 locations in each of measurements conducted under the condition that the linear pressure between the heating roll 5 and the press roll 6 was 0 N/10 mm, 1.5 N/10 mm, 4.6 N/10 mm, 7.7 N/10 mm or 10.8 N/10 mm.

Figure 9:
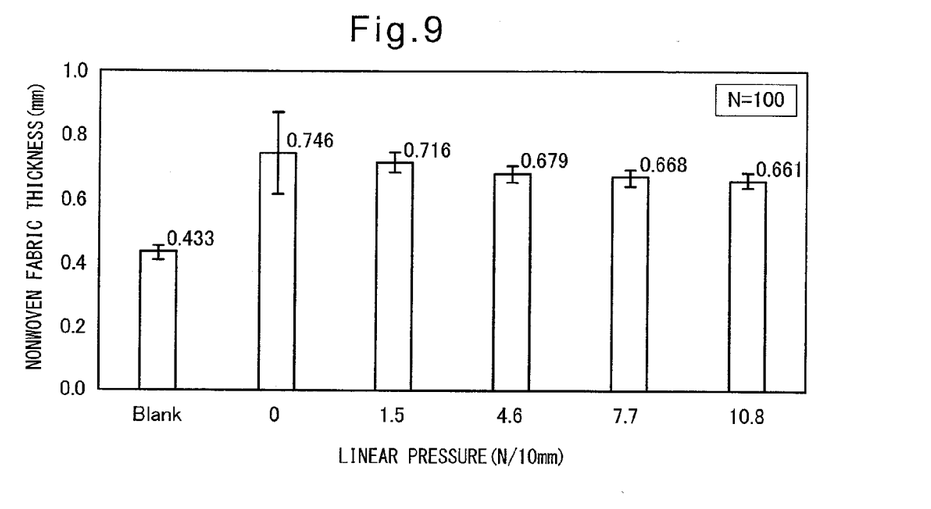
FIG. 9 is a graph showing the relationship between the linear pressure applied by a heating roll and press roll, and the thickness of a nonwoven fabric compressed by the heating roll and press roll.

The height of each bar in the graph of FIG. 9 represents the average value of the thickness of the nonwoven fabric, and the length of each mark shown above the top end of the bar in the longitudinal direction indicates the variation in the thickness of the nonwoven fabric. A larger length of the mark shown above the top end of the bar in the longitudinal direction represents a larger variation in the thickness of the nonwoven fabric. The denotation "Blank" represents the thickness of a non-stretched nonwoven fabric.

These results indicate that stretching a nonwoven fabric increases variation in the thickness of the nonwoven fabric, and that even if there is a large variation in the thickness of the nonwoven fabric 7 due to stretching, compressing the nonwoven fabric 7 between the heating roll 5 and the press roll 6 reduces variation in the thickness. This thickness variation is caused by wrinkles in the machine direction of the stretched nonwoven fabric. Consequently, compressing the nonwoven fabric 7 between the heating roll 5 and the press roll 6 resulted in fewer wrinkles in the machine direction of the stretched nonwoven fabric and more uniformity of the stretched nonwoven fabric.

The relationship between the linear pressure applied by the heating roll 5 and press roll 6, and the width of the nonwoven fabric 7 compressed by the heating roll 5 and press roll 6, will now be explained with reference to the graph in FIG. 11. The nonwoven fabric stretched at a transport ratio of 1.02 as described above was passed between the heating roll 5 and the press roll 6, and the width of the nonwoven fabric 7 was measured.

As shown in FIG. 10, the nonwoven fabric 7 contacting the outer peripheral surface 51 of the heating roll 5 was photographed with a video camera, and the width W of the nonwoven fabric 7 was calculated from the photographed image, to measure the width of the nonwoven fabric 7. The nonwoven fabric 7 was compressed using the heating roller 5 which was unheated. The width of the nonwoven fabric was examined at 100 locations in each of measurements conducted under the condition that the linear pressure between the heating roll 5 and the press roll 6 was 0 N/10 mm, 1.5 N/10 mm, 4.6 N/10 mm, 7.7 N/10 mm or 10.8 N/10 mm.

Figure 11:
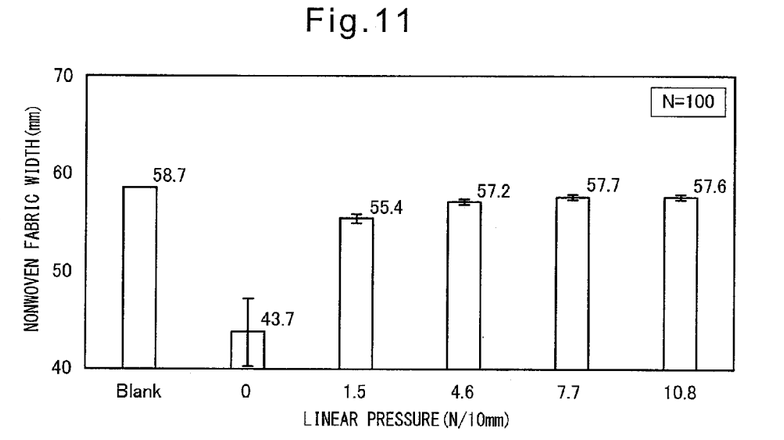
FIG. 11 is a graph showing the relationship between the linear pressure applied by a heating roll and press roll, and the width of a nonwoven fabric 7 compressed by the heating roll and press roll.

The height of each bar in the graph of FIG. 11 represents the average value of the width of the nonwoven fabric, and the length of each mark shown above the top end of the bar in the longitudinal direction indicates the variation in the width of the nonwoven fabric. A larger length of the mark shown above the top end of the bar in the longitudinal direction represents a larger variation in the width of the nonwoven fabric. The denotation "Blank" represents the width of a non-stretched nonwoven fabric.

These results indicate that stretching a nonwoven fabric decreases the width of the nonwoven fabric and increases variation in the width of the nonwoven fabric, and that even if there is a large variation in the width of the nonwoven fabric 7 due to stretching, applying pressure to the nonwoven fabric 7 between the heating roll 5 and the press roll 6 reduces variation in the width. In addition, it is seen that if the linear pressure between the heating roll 5 and the press roll 6 is at least 1.5 N/10 mm, the width of the nonwoven fabric narrowed by stretching approaches the width of the nonwoven fabric before stretching. The decrease and variation in width are caused by wrinkles in the machine direction of the stretched nonwoven fabric. Consequently, compressing the nonwoven fabric 7 between the heating roll 5 and the press roll 6 resulted in fewer wrinkles in the machine direction of the stretched nonwoven fabric and more uniformity of the stretched nonwoven fabric.

The nonwoven fabric 7 was compressed in the thickness direction of the nonwoven fabric 7 by the heating roll 5 and press roll 6, but instead only the stretched section 71 of the nonwoven fabric 7 may be compressed in the thickness direction of the nonwoven fabric 7 by the heating roll 5 and press roll 6. This allows the unstretched sections 72 of the nonwoven fabric 7 to be isolated from the effects of the pressure applied by the heating roll 5 and press roll 6. For example, if the widths of the heating roll 5 and press roll 6, or the width of the heating roll 5 or the width of the press roll 6, are the same as the width of the stretched section 71 of the nonwoven fabric 7, then it will be possible to compress only the stretched section 71 of the nonwoven fabric 7 in the thickness direction.

The heating roll 5 heats the nonwoven fabric 7. This will allow the width of the stretched nonwoven fabric to be roughly equal to the width of the nonwoven fabric before stretching, will allow the shape, such as width and thickness, as well as the density and strength of the stretched nonwoven fabric 7 to be uniform, and will allow the stretched nonwoven fabric to be stably transported and stably processed in a subsequent step.

The temperature of the heating roll 5 is preferably a temperature of not lower than 40° C. and not higher than the melting point of the fibers of the nonwoven fabric 7, and it is more preferably 40° C. to 120° C. and even more preferably 80° C. to 120° C. If the temperature of the heating roll 5 is lower than 40° C., there may be no effect of heating the nonwoven fabric 7 by the heating roll 5, and if the temperature of the heating roll 5 is higher than the melting point of the fibers of the nonwoven fabric 7, the fibers of the nonwoven fabric 7 may melt, causing contraction of the nonwoven fabric 7.

The relationship between the temperature of the heating roll 5 and the thickness of the nonwoven fabric 7 heated by the heating roll 5 will now be explained with reference to the graph in FIG. 12. The nonwoven fabric stretched at a transport ratio of 1.02 as described above was passed between the heating roll 5 and the press roll 6, and the thickness of the nonwoven fabric 7 was measured. The thickness of the nonwoven fabric 7 was measured by the same method used for examination of the relationship between the linear pressure applied by the heating roll 5 and press roll 6 and the thickness of the nonwoven fabric 7. The linear pressure between the heating roll 5 and the press roll 6 was 10.8 N/10 mm. The thickness of the nonwoven fabric was examined at 100 locations in each of measurements conducted under the condition that the temperature of the heating roll 5 was 20° C., 40° C., 60° C., 80° C., 100° C., 120° C. or 140° C.

Figure 12:
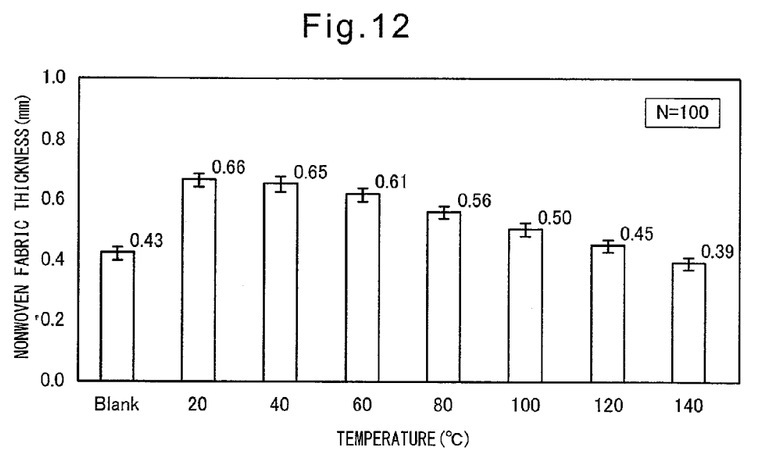
FIG. 12 is a graph showing the relationship between the temperature of a heating roll and the thickness of a nonwoven fabric heated by the heating roll.

The height of each bar in the graph of FIG. 12 represents the average value of the thickness of the nonwoven fabric, and the length of each mark shown above the top end of the bar in the longitudinal direction indicates the variation in the thickness of the nonwoven fabric. The denotation "Blank" represents the thickness of a non-stretched nonwoven fabric.

These results indicate that heating the nonwoven fabric 7 by the heating roller 5 reduces the thickness of the nonwoven fabric, so that it is near the thickness of the nonwoven fabric before stretching. It is seen, in particular, that if the temperature of the heating roll 5 is 120° C., the thickness of the nonwoven fabric is roughly the same as, the thickness of the nonwoven fabric before stretching.

The relationship between the temperature of the heating roll 5 and the width of the nonwoven fabric 7 heated by the heating roll 5 will now be explained with reference to the graph in FIG. 13. The nonwoven fabric stretched at a transport ratio of 1.02 as described above was passed between the heating roll 5 and the press roll 6, and the width of the nonwoven fabric 7 was measured. The width of the nonwoven fabric 7 was measured by the same method used for examination of the relationship between the linear pressure applied by the heating roll 5 and press roll 6 and the width of the nonwoven fabric 7. The linear pressure between the heating roll 5 and the press roll 6 was 10.8 N/10 mm. The width of the nonwoven fabric was examined at 100 locations in each of measurements conducted under the condition that the temperature of the heating roll 5 was 20° C., 40° C., 60° C., 80° C., 100° C., 120° C. or 140° C.

Figure 13:
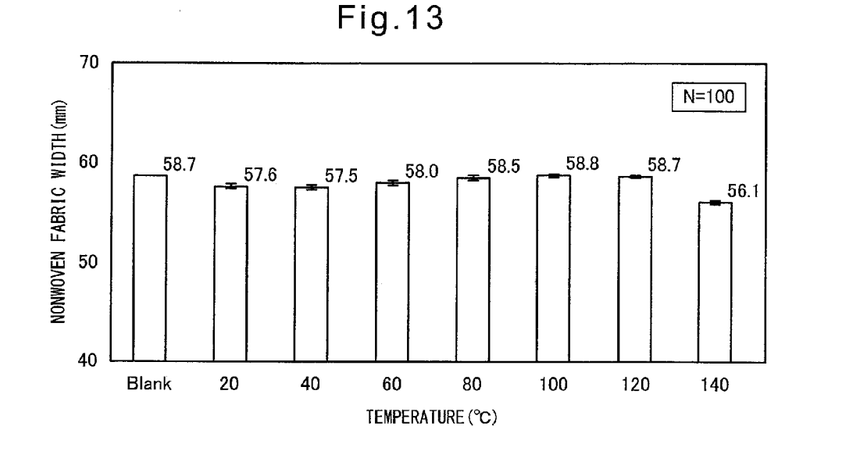
FIG. 13 is a graph showing the relationship between the temperature of a heating roll and the width of a nonwoven fabric heated by the heating roll.

The height of each bar in the graph of FIG. 13 represents the average value of the width of the nonwoven fabric, and the length of each mark shown above the top end of the bar in the longitudinal direction indicates the variation in the width of the nonwoven fabric. The denotation "Blank" represents the width of a non-stretched nonwoven fabric.

These results indicate that heating the nonwoven fabric 7 by the heating roller 5 increases the width of the nonwoven fabric, so that it is near the width of the nonwoven fabric before stretching. It is seen, in particular, that if the temperature of the heating roll 5 is 80° C. to 120° C., the width of the nonwoven fabric is roughly the same as the width of the nonwoven fabric before stretching. The reduced width of the nonwoven fabric, which occurred when the temperature of the heating roll 5 was 140° C., is attributed to melting of some of the fibers of the nonwoven fabric.

Figure 14:
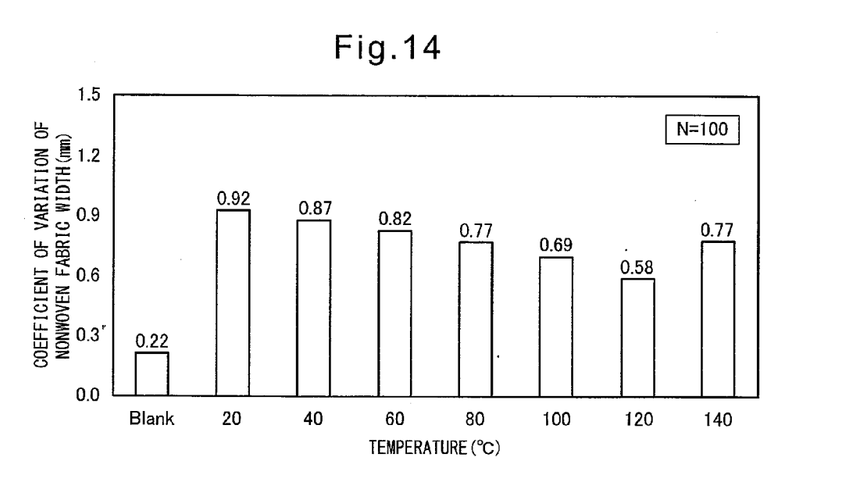
FIG. 14 is a graph showing the relationship between the temperature of a heating roll and the coefficient of variation for the width of a nonwoven fabric heated by the heating roll.

FIG. 14 shows the coefficient of variation for the width of the nonwoven fabric, which was obtained when the relationship between the temperature of the heating roll 5 and the width of the nonwoven fabric 7 heated by the heating roll 5 was examined. "Blank" represents the coefficient of variation for the width of a non-stretched nonwoven fabric.

These results indicate that heating the nonwoven fabric 7 by the heating roller 5 results in a smaller coefficient of variation for the width of the nonwoven fabric. This shows that the nonwoven fabric 7 is rendered uniform by heating the nonwoven fabric 7 by the heating roller 5. Also, it is seen that the coefficient of variation for the width of the nonwoven fabric decreases as the temperature of the heating roller 5 increases. The increased coefficient of variation for the width of the nonwoven fabric, which occurred when the temperature of the heating roll 5 was 140° C., is attributed to melting of some of the fibers of the nonwoven fabric.

The relationship between the temperature of the heating roll 5 and the strength at 50% elongation of the nonwoven fabric 7 heated by the heating roll 5 will now be explained with reference to the graph in FIG. 15. The nonwoven fabric stretched at a transport ratio of 1.02 as described above was passed between the heating roll 5 and the press roll 6, a test sample was produced from the passed nonwoven fabric, and the test sample was used to measure the strength at 50% elongation of the nonwoven fabric 7. The linear pressure between the heating roll 5 and the press roll 6 was 10.8 N/10 mm. Five test samples, which were produced under the condition that the temperature of the heating roll 5 was 20° C., 40° C., 60° C., 80° C., 100° C., 120° C. or 140° C., were used in each of measurements of the strength at 50% elongation of the nonwoven fabric.

The nonwoven fabric 7 passed between the heating roll 5 and the press roll 6 was cut at 50 mm intervals in the cross-machine direction, to produce test samples with 50 mm widths. In each of the measurements, 50 mm-wide five test samples were used to measure the tensile strength at 50% elongation, using a tensile tester equipped with a load cell with a maximum load capacity of 50 N (AGS-1kNG Autograph, product of Shimadzu Corp.), under conditions with a clamp distance of 40 mm and a pull rate of 40 mm/min.

Figure 15:
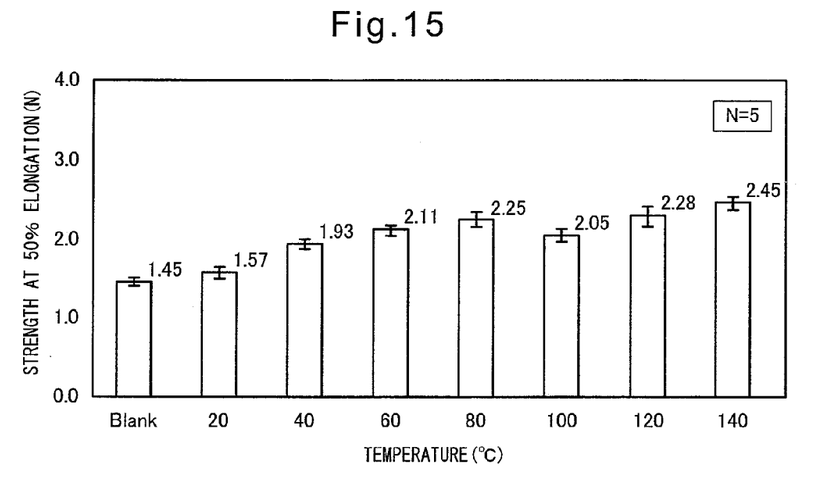
FIG. 15 is a graph showing the relationship between the temperature of a heating roll and the strength at 50% elongation of a nonwoven fabric heated by the heating roll.

The height of each bar in the graph of FIG. 15 represents the average value of the strength at 50% elongation for the nonwoven fabric, and the length of each mark shown above the top end of the bar in the longitudinal direction indicates the variation in the strength at 50% elongation for the nonwoven fabric. Also, "Blank" denotes the strength at 50% elongation of a nonwoven fabric that was not heated and compressed with the heating roll 5 and press roll 6.

These results indicate that heating the nonwoven fabric 7 by the heating roller 5 results in a larger strength at 50% elongation for the nonwoven fabric. This demonstrates that heating the nonwoven fabric does not result in reduced strength of the nonwoven fabric or increased variation in the strength. In addition, since heating the nonwoven fabric 7 by the heating roller 5 increases the strength, the transport property of the nonwoven fabric 7 increases.

The relationship between the temperature of the heating roll 5 and the S2 elongation, maximum strength and strain at maximum strength for the nonwoven fabric 7 heated by the heating roll 5 will now be explained with reference to the graphs in FIGS. 16 to 18. The nonwoven fabric stretched at a transport ratio of 1.02 as described above was passed between the heating roll 5 and the press roll 6, a test sample was produced from the passed nonwoven fabric, and the test sample was used to measure the S2 elongation, maximum strength and strain at maximum strength for the nonwoven fabric 7. The linear pressure between the heating roll 5 and the press roll 6 was 10.8 N/10 mm. Five test samples, which were produced under the condition that the temperature of the heating roll 5 was 20° C., 40° C., 60° C., 80° C., 100° C., 120° C. or 140° C., were used in each of measurements of the S2 elongation, maximum strength and strain at maximum strength for the nonwoven fabric.

The nonwoven fabric 7 passed between the heating roll 5 and the press roll 6 was cut at 50 mm intervals in the cross-machine direction, to produce test samples with 50 mm widths. In each of the measurements, 50 mm-wide five test samples were used to measure the elongation and tensile strength, using a tensile tester equipped with a load cell with a maximum load capacity of 50 N (AGS-1kNG Autograph, product of Shimadzu Corp.), under conditions with a clamp distance of 40 mm and a pull rate of 40 mm/min. Also, the S2 elongation, maximum strength and strain at maximum strength were calculated from the results for the measured elongations and tensile strengths of the test samples.

Figure 19:
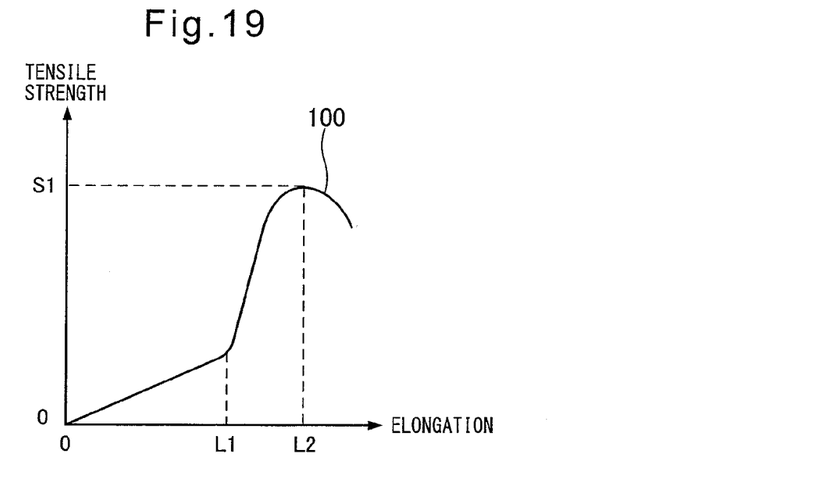
FIG. 19 is a graph for illustration of S2 elongation, maximum strength and strain at maximum strength.

The S2 elongation, maximum strength and strain at maximum strength will now be explained with reference to FIG. 19. FIG. 19 is a graph showing an example of measurement results for tensile strength of a test sample. The abscissa of the graph of FIG. 19 represents elongation of the test sample, and the ordinate represents tensile strength of the test sample. The slope of the elongation-tensile strength curve 100 for the test sample changes after the test sample has elongated to a length of L1. This shows that, up to elongation to a length of L1, the test sample elongates due to elongation of fibers that have stretchability due to stretching, while at elongation after L1, the test sample elongates due to breakdown of binding between the fibers and deformation of the fibers themselves. The S2 elongation is calculated by dividing the value of L1 by the distance between the clamps, i.e. 40 mm. Also, S1 is the maximum tensile strength in the elongation-tensile strength curve 100 for the test sample. The value of S1 is the maximum strength. In addition, the strain at the maximum strength is calculated by dividing the value of L2, which corresponds to the elongation of the test sample at the maximum tensile strength (S1), by the distance between clamps, i.e. 40 mm.

Figure 16:
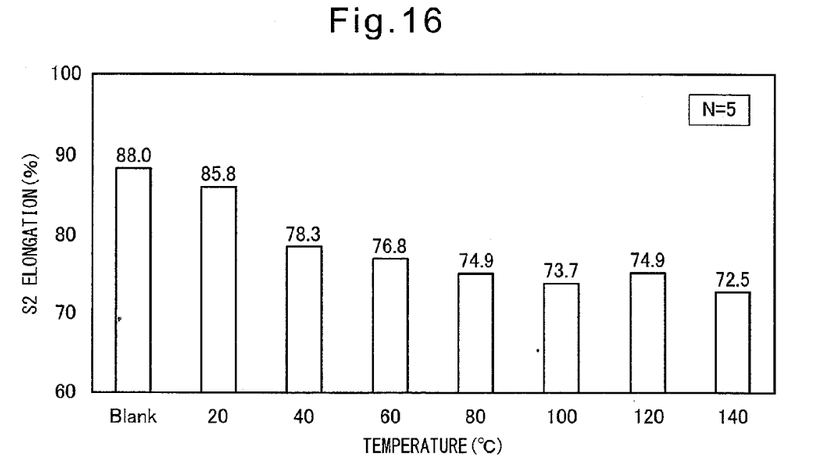
FIG. 16 is a graph showing the relationship between the temperature of a heating roll and the S2 elongation of a nonwoven fabric heated by the heating roll.

The height of each bar in the graph in FIG. 16 represents the average value of the S2 elongation for the nonwoven fabric. The denotation "Blank" represents the S2 elongation of a non-stretched nonwoven fabric. These results indicate that heating the nonwoven fabric 7 by the heating roller 5 results in a smaller S2 elongation of the nonwoven fabric. This indicates that controlling the temperature of the heating roller 5 allows the S2 elongation of the nonwoven fabric to be adjusted. Incidentally, although heating with the heating roller 5 results in reduced S2 elongation of the nonwoven fabric, the value of the reduced S2 elongation is within the allowable range from the viewpoint of use in a product such as an absorbent article.

Figure 17:
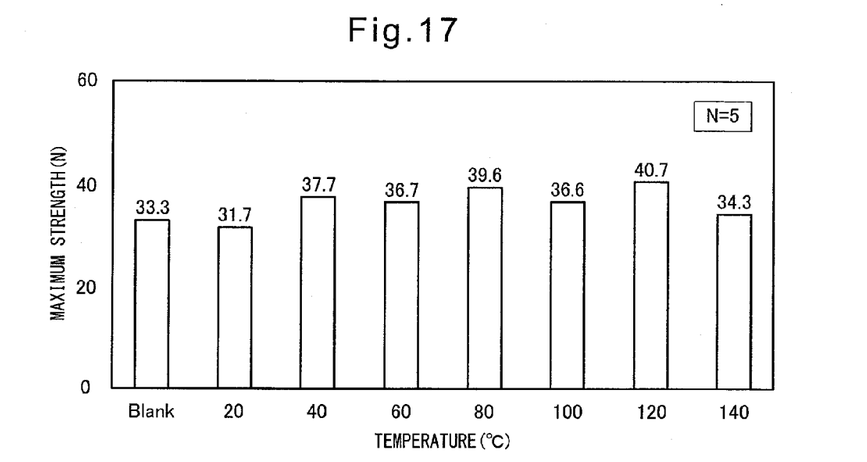
FIG. 17 is a graph showing the relationship between the temperature of a heating roll and the maximum strength of a nonwoven fabric heated by the heating roll.

The height of each bar in the graph in FIG. 17 represents the average value of the maximum strength of the nonwoven fabric. Also, "Blank" denotes the maximum strength of a nonwoven fabric that was not heated and compressed with the heating roll 5 and press roll 6. These results indicate that heating the nonwoven fabric 7 by the heating roller 5 results in a higher maximum strength of the nonwoven fabric. This shows that the strength of the nonwoven fabric is not reduced by heating the nonwoven fabric using the heating roller 5.

Figure 18:
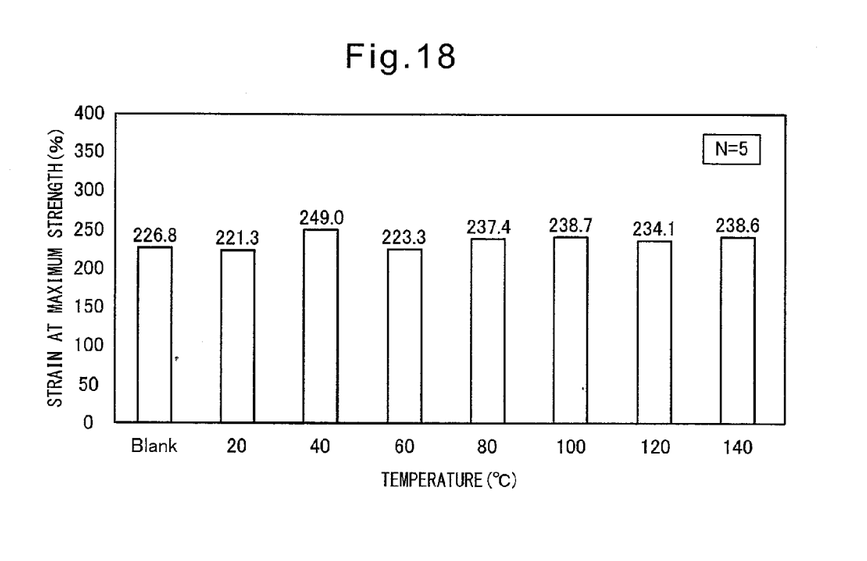
FIG. 18 is a graph showing the relationship between the temperature of a heating roll and the strain at maximum strength of a nonwoven fabric heated by the heating roll.

The height of each bar in the graph in FIG. 18 represents the average value of strain at maximum strength for the nonwoven fabric. Also, "Blank" denotes the strain at maximum strength for a nonwoven fabric that was not heated and compressed with the heating roll 5 and press roll 6. These results indicate that the strain at maximum strength of the nonwoven fabric is not significantly reduced even by heating the nonwoven fabric 7 using the heating roller 5.

Incidentally, although the nonwoven fabric 7 was compressed and heated by the heating roll 5 and press roll 6, compression alone may be carried out on the nonwoven fabric 7 by the heating roll 5 and press roll 6. This will likewise allow the shape, such as width and thickness of the stretched nonwoven fabric 7 to be uniform, and allows the stretched nonwoven fabric 7 to be stably transported and stably processed in a subsequent step.

Alternatively, the press roll 6 may also be heated to heat the nonwoven fabric 7 by the heating roll 5 and press roll 6.

Incidentally, although the nonwoven fabric 7 was heated by the heating roll 5 and press roll 6, alternatively, only the stretched section 71 of the nonwoven fabric 7 may be heated by the heating roll 5 and press roll 6. This allows the unstretched sections 72 of the nonwoven fabric 7 to be isolated from the effects of the heat applied by the heating roll 5 and press roll 6. For example, if the widths of the heating roll 5 and press roll 6, or the width of the heating roll 5 or the width of the press roll 6, are the same as the width of the stretched section 71 of the nonwoven fabric 7, then it will be possible to heat only the stretched section 71 of the nonwoven fabric 7.

Figure 20:
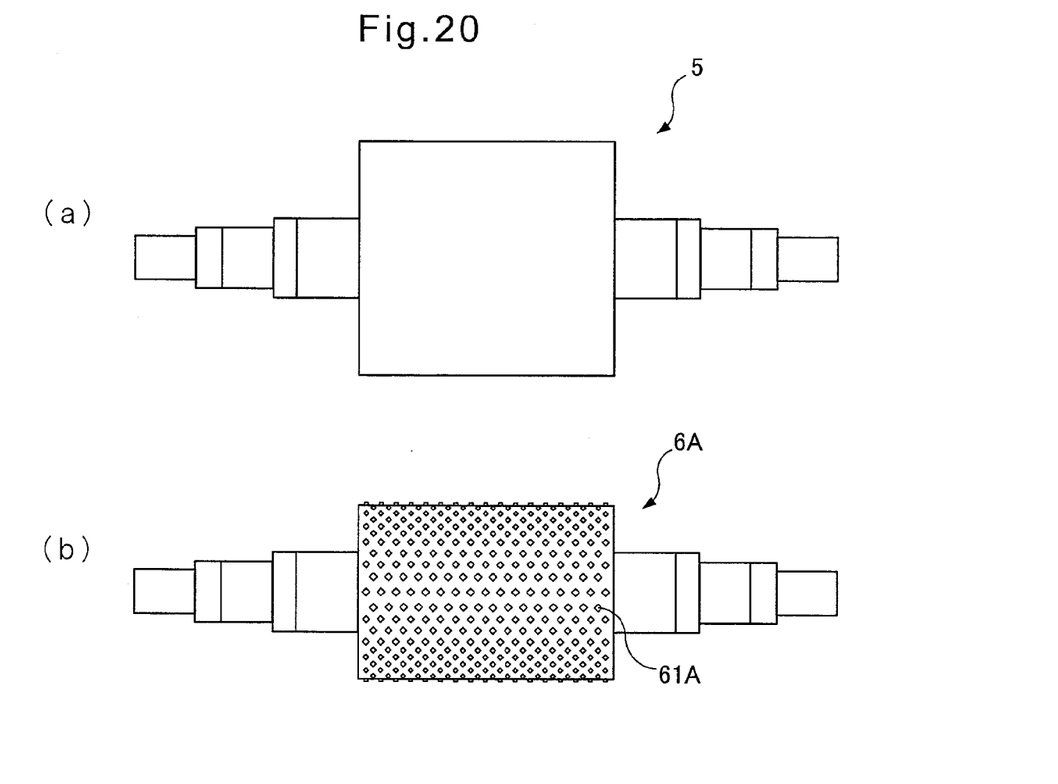
FIG. 20 is a diagram showing an example of a combination of a flat heating roll and a patterned press roll.

Also, although the heating roll 5 and press roll 6 were flat rolls, either the heating roll or press roll may be a patterned roll, with the other being a flat roll. A patterned roll is a roll having dot-like convex parts on the outer peripheral surface. For example, the heating roll 5 may be a flat roll as shown in FIG. 20(a), and the press roll 6A may be a patterned roll as shown in FIG. 20(b). A plurality of convex parts 61A with rhomboid cross-sections on the plane along the outer peripheral surface are arranged on the outer peripheral surface of the press roll 6A. The shapes of the cross-sections of the convex parts on the plane along the outer peripheral surface are not limited to being rhomboid, and may instead be rectangular-shaped, square-shaped, circular-shaped, elliptical-shaped or star-shaped.

When the nonwoven fabric is compressed in the thickness direction by passing between the press roll 6A and the heating roll 5, the nonwoven fabric is embossed by the convex parts 61A of the press roll 6A. Thus, even when a combination of a flat roll and a patterned roll is used for embossing, it is possible to obtain a similar effect as the effect obtained by compression in the thickness direction by the heating roll 5 and press roll 6, which are both flat rolls. Incidentally, the heating roll may be a patterned roll and the press roll may be a flat roll.

The stretching apparatus may also be provided with a separate heating roll and press roll in addition to the heating roll 5 and press roll 6, for further compression or compression and heating of the nonwoven fabric compressed or compressed and heated by the heating roll 5 and the press roll 6. This will often allow a greater effect to be obtained by compression or compression and heating of the stretched nonwoven fabric.

The explanation above is merely an example, and the invention is in no way restricted by the described embodiment.

EXPLANATION OF SYMBOLS

1 Stretching apparatus
2 Transport roll
3 Upper stretching roll
4 Lower stretching roll
5 Heating roll
6, 6A Press rolls
7 Nonwoven fabric
32 Convex part of upper stretching roll
41 Convexity-formed section of lower stretching roll
42 Non-convexity-formed section of lower stretching roll
45 Convex part of lower stretching roll
51 Outer peripheral surface of heating roll
61A Convex part of press roll
71 Stretched section of nonwoven fabric
72 Unstretched section of nonwoven fabric
73 Top side of nonwoven fabric
100 Elongation-tensile strength curve of test sample

The invention claimed is:

1. A method for producing a stretchable sheet from a nonwoven fabric comprising extensible fibers and stretched fibers, the method comprising;
   a step of stretching the nonwoven fabric in the cross-machine direction perpendicular to the machine direction in which the nonwoven fabric is transported between two stretching rolls having teeth and grooves extending in a rotational direction thereof, without holding both peripheral edge portions of the nonwoven fabric, to form the stretched nonwoven fabric having wrinkles extending in the machine direction; and thereafter
   a step of compressing the nonwoven fabric stretched in the step of stretching the nonwoven fabric, in the thickness direction of the nonwoven fabric while being heated, to reduce the thickness of the stretched nonwoven fabric and the height of the wrinkles of the stretched nonwoven fabric, to thereby make the thickness of the stretched nonwoven fabric uniform.

2. The method for producing a stretchable sheet according to claim 1, wherein in the step of compressing the nonwoven fabric, the nonwoven fabric is compressed at a linear pressure of 1 to 100 N/10 mm.

3. The method for producing a stretchable sheet according to claim 2, wherein in the step of stretching the nonwoven fabric, a portion of the nonwoven fabric is stretched, and in the step of compressing the nonwoven fabric, only the stretched portion of the nonwoven fabric is compressed.

4. The method for producing a stretchable sheet according to claim 3, wherein in the step of compressing the nonwoven fabric, the nonwoven fabric is compressed while being heated.

5. The method for producing a stretchable sheet according to claim 4, wherein in the step of compressing the nonwoven fabric, the nonwoven fabric is heated at a temperature of 40° C. to 120° C.

6. The method for producing a stretchable sheet according to claim 3, which further comprises, after the step of compressing the nonwoven fabric, a step of compressing the nonwoven fabric in the thickness direction of the nonwoven fabric.

7. The method for producing a stretchable sheet according to claim 2, wherein in the step of compressing the nonwoven fabric, the nonwoven fabric is compressed while being heated.

8. The method for producing a stretchable sheet according to claim 7, wherein in the step of compressing the nonwoven fabric, the nonwoven fabric is heated at a temperature of 40° C. to 120° C.

9. The method for producing a stretchable sheet according to claim 7, which further comprises, after the step of compressing the nonwoven fabric, a step of compressing the nonwoven fabric in the thickness direction of the nonwoven fabric.

10. The method for producing a stretchable sheet according to claim 2, which further comprises, after the step of compressing the nonwoven fabric, a step of compressing the nonwoven fabric in the thickness direction of the nonwoven fabric.

11. The method for producing a stretchable sheet according to claim 1, wherein in the step of stretching the nonwoven fabric, a portion of the nonwoven fabric is stretched, and in the step of compressing the nonwoven fabric, only the stretched portion of the nonwoven fabric is compressed.

12. The method for producing a stretchable sheet according to claim 11, wherein in the step of compressing the nonwoven fabric, the nonwoven fabric is compressed while being heated.

13. The method for producing stretchable sheet according to claim 12, wherein in the step of compressing the nonwoven fabric, the nonwoven fabric is heated at a temperature of 40° C. to 120° C.

14. The method for producing a stretchable sheet according to claim 11, which further comprises, after the step of compressing the nonwoven fabric, a step of compressing the nonwoven fabric in the thickness direction of the nonwoven fabric.

15. The method for producing a stretchable sheet according to claim 1, wherein in the step of compressing the nonwoven fabric, the nonwoven fabric is heated at a temperature of 40° C. to 120° C.

16. The method for producing a stretchable sheet according to claim 1, which further comprises, after the step of compressing the nonwoven fabric, a step of compressing the nonwoven fabric in the thickness direction of the nonwoven fabric.

17. The method for producing a stretchable sheet according to claim 1, wherein in the step of compressing the nonwoven fabric, the nonwoven fabric is compressed in the thickness direction of the nonwoven fabric by a pair of flat rolls, or by a pattern roll and a flat roll.

18. The method for producing a stretchable sheet according to claim 1, wherein in the step of stretching the nonwoven fabric, the nonwoven fabric is stretched in the cross-machine direction by passing through a gap between a pair of rolls, each of which has convex parts formed on the outer peripheral surface and extending in the rotational direction, the convex parts of the rolls being engaged with each other so that the rolls rotate.

19. The method for producing a stretchable sheet according to claim 1, wherein the nonwoven fabric is passed through transporting rolls before the stretching rolls so as to wind the nonwoven fabric around one of the stretching rolls.

* * * * *